US009949450B2

(12) United States Patent
Richings, Sr. et al.

(10) Patent No.: US 9,949,450 B2
(45) Date of Patent: Apr. 24, 2018

(54) SOIL MOISTURE PROBE AND SYSTEM WITH TEMPERATURE ADJUSTMENT

(71) Applicant: MorpH2O Water Management, LLC, Ogden, UT (US)

(72) Inventors: Jon Richings, Sr., Springville, UT (US); Scott Martin, West Valley City, UT (US)

(73) Assignee: MorpH2O Water Management, LLC, Ogden, UT (US)

(*) Notice: Subject to any disclaimer, the term of this patent is extended or adjusted under 35 U.S.C. 154(b) by 41 days.

(21) Appl. No.: 14/921,978

(22) Filed: Oct. 23, 2015

(65) Prior Publication Data

US 2016/0183484 A1 Jun. 30, 2016

Related U.S. Application Data

(60) Provisional application No. 62/237,986, filed on Oct. 6, 2015, provisional application No. 62/074,156, filed on Nov. 3, 2014.

(51) Int. Cl.
A01G 25/16 (2006.01)
G01N 33/24 (2006.01)

(52) U.S. Cl.
CPC ......... A01G 25/167 (2013.01); G01N 33/246 (2013.01)

(58) Field of Classification Search
None
See application file for complete search history.

(56) References Cited

U.S. PATENT DOCUMENTS

| 3,581,197 A | 5/1971 | Morey, Jr. |
| 3,771,548 A | 11/1973 | Rauchwerger |
| 3,968,428 A | 7/1976 | Numoto |
| 3,982,177 A | 9/1976 | Walker et al. |
| 4,137,931 A | 2/1979 | Hasenbeck |
| 4,197,866 A * | 4/1980 | Neal ...................... A01G 25/16 137/1 |
| 4,288,742 A | 9/1981 | Walsh |

(Continued)

OTHER PUBLICATIONS

"PCapØ2 —Capacitance-to-Digital Converter with integrated Signal Processor", http://www.acam.de/products/picocap/pcapO2/?gclid=CjwKEAjwv8iwBRC35-_e8aPqwCESJAB8khP9K4uQIpP-eDNoK_SWIGXyG1uzVOK_wglv4YTn1s4SpxoCzWvw_wcB.

Primary Examiner — Mohammad Ali
Assistant Examiner — Bernard G Lindsay
(74) Attorney, Agent, or Firm — Thorpe North & Western, LLP.

(57) ABSTRACT

A plurality of wireless transmitters tethered to a plurality of soil moisture probes, each of said probes having first and second elongate conductive materials encapsulated in a non-conductive substrate, coupled to a power source and configured to be placed in the soil to form a capacitor. An irrigation control box is equipped with a receiver and a processor coupled to a plurality of irrigation control valves, each irrigation control valve corresponding to an irrigation zone wherein at least one probe is placed. The processor converts signal data received from the plurality of transmitters into a soil moisture value and (i) opens a control valve corresponding to the zone to which the probe corresponds upon detecting that the soil moisture value in the zone has dropped below a threshold value and (ii) closes the control valve upon detecting that the soil moisture value has raised above a threshold value.

17 Claims, 12 Drawing Sheets

(56) References Cited

U.S. PATENT DOCUMENTS

| | | | |
|---|---|---|---|
| 4,540,936 | A | 9/1985 | Walsh |
| 4,657,039 | A | 4/1987 | Bireley et al. |
| 4,850,386 | A | 7/1989 | Bireley |
| 4,909,070 | A | 3/1990 | Smith |
| 4,931,775 | A | 6/1990 | Sheriff |
| 4,952,868 | A * | 8/1990 | Scherer, III .......... A01G 25/167 137/78.3 |
| 5,148,125 | A | 9/1992 | Woodhead et al. |
| 5,260,666 | A | 11/1993 | Dishman et al. |
| 5,341,673 | A | 8/1994 | Burns et al. |
| 5,424,649 | A | 6/1995 | Gluck et al. |
| 5,442,293 | A | 8/1995 | Lange |
| 5,445,178 | A | 8/1995 | Feuer |
| 5,479,104 | A * | 12/1995 | Cambell ............... G01N 27/048 324/663 |
| 5,546,974 | A | 8/1996 | Bireley |
| 5,740,031 | A | 4/1998 | Gagnon |
| 5,749,521 | A * | 5/1998 | Lattery ................ A01G 25/167 137/78.3 |
| 5,859,536 | A | 1/1999 | Stockton |
| 6,060,889 | A | 5/2000 | Rocker |
| 6,975,245 | B1 | 12/2005 | Slater et al. |
| 7,042,234 | B2 | 5/2006 | Buss |
| 7,170,302 | B2 | 1/2007 | Lee |
| 7,482,820 | B1 | 1/2009 | Campbell |
| 7,535,237 | B1 | 5/2009 | Campbell |
| 7,836,910 | B2 | 11/2010 | Dresselhaus et al. |
| 7,884,620 | B2 | 2/2011 | Campbell |
| 8,035,403 | B1 | 10/2011 | Campbell et al. |
| 8,089,287 | B2 | 1/2012 | Izadnegandar |
| 8,104,498 | B2 | 1/2012 | Dresselhaus et al. |
| 8,225,810 | B2 | 7/2012 | Blanchard |
| 8,302,881 | B1 | 11/2012 | Campbell et al. |
| 8,308,077 | B1 | 11/2012 | Campbell et al. |
| 8,366,017 | B1 | 2/2013 | Campbell et al. |
| 8,368,529 | B1 | 2/2013 | Campbell et al. |
| 8,374,553 | B1 | 2/2013 | Campbell et al. |
| 8,565,927 | B1 | 10/2013 | Campbell et al. |
| 8,671,969 | B2 | 3/2014 | Dresselhaus et al. |
| 8,682,493 | B1 | 3/2014 | Campbell et al. |
| 2008/0199359 | A1 | 8/2008 | Davis et al. |
| 2008/0211521 | A1 * | 9/2008 | Lock .................... G01N 27/048 324/696 |
| 2009/0134889 | A1 | 5/2009 | Gunsay |
| 2010/0277185 | A1 | 11/2010 | Hughes |
| 2012/0319704 | A1 * | 12/2012 | Skaling ................ G01N 33/246 324/658 |
| 2013/0200905 | A1 | 8/2013 | Rhodes et al. |
| 2013/0341420 | A1 | 12/2013 | Lister et al. |
| 2014/0129039 | A1 * | 5/2014 | Olive-Chahinian ... A01G 25/16 700/284 |
| 2015/0040473 | A1 * | 2/2015 | Lankford ............... A01G 1/001 47/58.1 SC |
| 2015/0285752 | A1 * | 10/2015 | Kozicki ............. A01D 41/1243 324/649 |

* cited by examiner

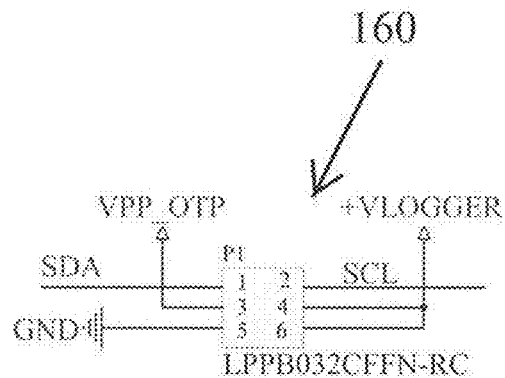
| Sensor debug connector | PicoProg v2.0 pin | PicoProg v2.0 signal |
|---|---|---|
| 1 | 1 | IIC_SDA |
| 2 | 7 | IIC_SCL |
| 3 | 5 | VCC_OTP |
| 4 | 14 | VCC_LEVEL |
| 5 | 3 | GND |
| 6 | 9 | VCC_3V3 |
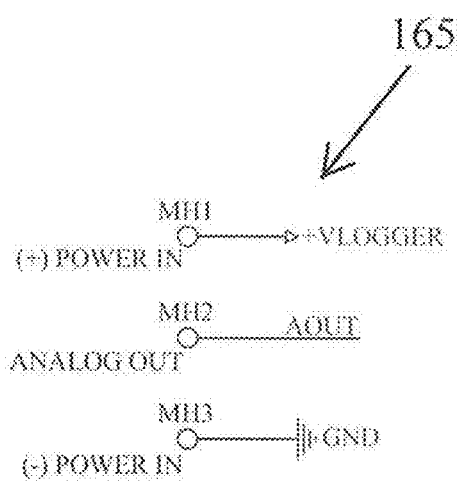
FIG.5

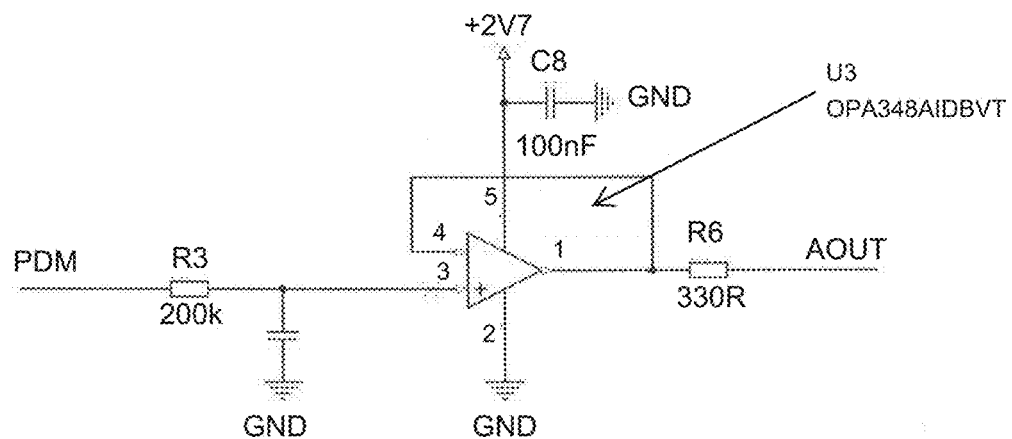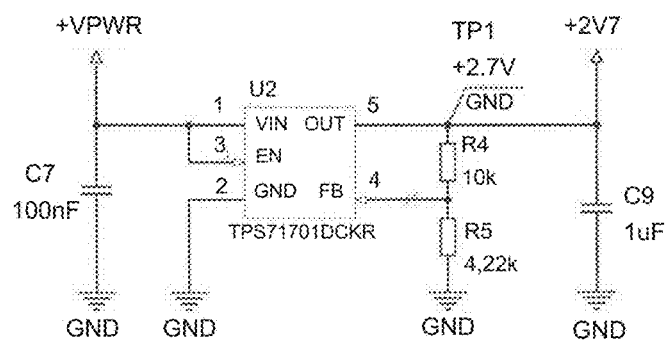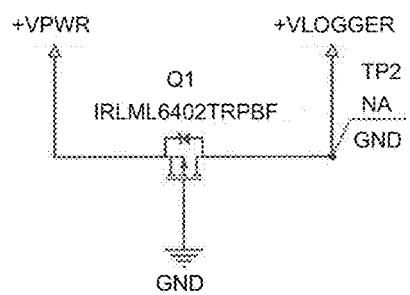
FIG. 7

SOIL MOISTURE PROBE AND SYSTEM WITH TEMPERATURE ADJUSTMENT

CLAIM OF PRIORITY

This application claims priority to U.S. Provisional Patent Application No. 62/237,986 entitled "Soil Moisture Probe" filed on Oct. 6, 2015 which is incorporated herein by this reference in its entirety and U.S. Provisional Patent Application No. 62/074,156 entitled "Probe Tethered to Transmitter" filed on Nov. 3, 2014 which is incorporated herein by this reference in its entirety.

FIELD OF THE INVENTION

This invention relates generally to monitoring subsurface conditions. Specifically, it relates to an improved apparatus and systems for monitoring and controlling subsurface soil moisture.

BACKGROUND

Water conservation is an increasingly important social issue as populations increase in urbanized areas and variable weather patterns create geographic areas of "water stress." Measuring soil moisture is important for agricultural applications to help farmers manage their irrigation systems more efficiently. Knowing the exact soil moisture conditions on their fields, not only are farmers able to generally use less water to grow a crop, they are also able to increase yields and the quality of the crop by improved management of soil moisture during critical plant growth stages. In urban and suburban areas, landscapes and residential lawns are using soil moisture sensors to interface with an irrigation controller. Connecting a soil moisture sensor to a simple irrigation clock will convert it into a "smart" irrigation controller that prevents irrigation cycles when the soil is already wet, e.g., following a recent rainfall event. In other situations, golf courses are using soil moisture sensors to increase the efficiency of their irrigation systems to prevent over-watering and leaching of fertilizers and other chemicals into the ground. Resistive/conductive sensors rely on the resistive/conductive property of moist soils and consist of at least two electrodes inserted into the soil and a means to measure the resistance/conductance between these electrodes. The resistive/conductive property of soils changes with its composition. Properties such as salinity and acidity greatly affect resistive/conductive readings and for this type of sensor to be effective, a comparative method is required to calibrate the sensor to the soil. Dielectric sensors consist of a known material that is located between at least two plate electrodes. The material becomes the dielectric of the sensor. The sensor is placed in contact with the soil to be measured and by contact the dielectric material becomes moist. The capacitance or resistance of the resultant sensor is measured. These types of sensors provide immunity to the composition of the soil but suffer from a limited useful life since the dielectric material degrades with time. Additionally, these sensors suffer from slow response since the dielectric material takes time to reach the same moisture level as the surrounding soil. The present technology seeks to optimize the use of soil moisture sensors that interface with irrigation controllers to overcome deficiencies in prior art systems.

SUMMARY

In light of the problems and deficiencies inherent in the prior art, the present invention seeks to overcome these by providing methods, devices, and systems for a wireless transmitter tethered to a stand-alone soil moisture probe by a length of cable, said probe having first and second elongate conductive materials encapsulated in a non-conductive substrate, said first and second elongate materials coupled to a power source and configured to be placed in the soil to form a capacitor. The probe also has a soil moisture circuit encapsulated in the non-conductive substrate coupled to the power source, said circuit having an oscillator for applying an electrical stimulus to the first and second elongate conductive materials. In addition, a third elongate conductive material is encapsulated in the non-conductive substrate and disposed between the first and second elongate conductive materials, said third elongate material being coupled to the soil moisture circuit and conductively isolated from the first and second elongate conductive materials.

In another aspect of the technology, a method of using a plurality of probes to detect a capacitance value in soil in a plurality of irrigation zones is described, wherein at least one probe is located in each of the plurality of irrigation zones, and wherein each probe is tethered to a wireless transmitter configured to send a wireless signal to an irrigation control box. Transmitters transmit a wireless signal from each of the plurality of wireless transmitters to a receiver coupled to the irrigation control box which receives the plurality of signals from the plurality of wireless transmitters into a processor of the irrigation control box, said plurality of signals corresponding to the capacitance value in the soil measured in each one of the plurality of irrigation zones. The method includes converting the capacitance values to a soil moisture value and comparing the capacitance values to pre-determined upper and lower soil moisture threshold values. Upon detecting that a soil moisture value in an irrigation zone has dropped below a lower threshold value, an irrigation control valve is opened corresponding to the irrigation zone having the soil moisture value below the lower threshold value. Upon detecting that a soil moisture value in an irrigation zone has raised above an upper threshold value, the irrigation control valve corresponding to the irrigation zone having the soil moisture value above the upper threshold value is closed. In one aspect, the method includes creating a priority ranking of irrigation zones. Upon detection that the soil moisture value in more than one irrigation zones has dropped below a threshold value, the irrigation zones are ranked where the soil moisture value has dropped below the threshold value according to the priority ranking. The irrigation valve corresponding to the irrigation zone having the highest rank is opened. In another aspect, an ambient air temperature is taken proximate to an irrigation zone and upon detection that the ambient air temperature exceeds a threshold level, the upper and lower soil moisture threshold values are modified.

BRIEF DESCRIPTION OF THE FIGURES

To further clarify the above and other aspects of the present technology, a more particular description of the invention will be rendered by reference to specific aspects thereof which are illustrated in the appended drawings. It is appreciated that these drawings depict only typical aspects of the technology and are therefore not to be considered limiting of its scope. The drawings are not drawn to scale. The technology will be described and explained with additional specificity and detail through the use of the accompanying drawings in which:

FIG. 5 is a schematic of certain probe circuitry in accordance with one aspect of the technology;

FIG. 7 is a schematic of certain probe circuitry in accordance with one aspect of the technology;

FIG. 8a is a top perspective view of one side of a probe in accordance with one aspect of the technology;

FIG. 8b is a bottom perspective view of the probe shown in 8a;

DESCRIPTION OF THE TECHNOLOGY

Figure 1:
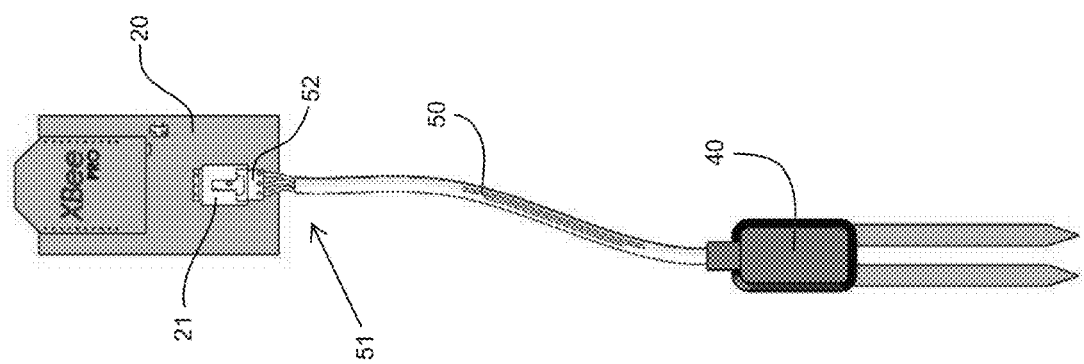
FIG. 1 is a front view of a transmitter tethered to a probe in accordance with one aspect of the technology.

The following detailed description of exemplary aspects of the technology makes reference to the accompanying drawings, which form a part hereof and in which are shown, by way of illustration, exemplary aspects in which the technology may be practiced. While these exemplary aspects are described in sufficient detail to enable those skilled in the art to practice the technology, it should be understood that other aspects may be realized and that various changes to the technology may be made without departing from the spirit and scope of the present invention. Thus, the following more detailed description of the aspects of the present technology is not intended to limit the scope of the invention, as claimed, but is presented for purposes of illustration only and not limitation to describe the features and characteristics of the present technology, to set forth the best mode of operation of the technology, and to sufficiently enable one skilled in the art to practice the invention.

The following detailed description and exemplary aspects of the invention will be further understood by reference to the accompanying drawings, wherein the elements and features of the invention are designated by numerals throughout.

The present technology in its various embodiments, some of which are depicted in the figures herein, can be broadly described as a wireless transmitter disposed within a housing configured for placement in a subsurface environment (e.g., soil) such that a top portion of the housing is generally flush with a top of the subsurface and is used in connection with an irrigation control system. A probe is detachably tethered to the wireless transmitter by way of a cable assembly. The probe is configured for placement within a subsurface environment, like soil, and is further configured to collect information related to the subsurface environment, including the volumetric water content (VWC) of an amount of soil that is within the "field of influence" of the probe. Advantageously, by tethering the probe to the wireless transmitter via a cable assembly, a single transmitter design may be employed with probes of varying lengths (e.g., 1 to 200 feet). In other words, a single transmitter design may be used with probes having varying cable lengths which reduces manufacturing costs. This allows the user to place the probe in a subsurface area that is subjected to traffic while placing the transmitter in an area that either receives less traffic or no traffic at all. This extends the life of the probe by not subjecting it to undue strain as it does not require a shallow placement in order to transmit a signal. In many instances it is desirable to centrally locate numerous transmitters in a single location but install probes in various remote locations. The variable cable assembly of the present technology permits such an application. It may also be desirable to place a transmitter in a low traffic area but place the probe in a subsurface area that is subject to high traffic. In this manner, the transmitter, which is more susceptible to inadvertent displacement by foot traffic (or other surface activities), may be placed out of the way while the subsurface probe is located in a desirable position. The cable system also permits orientation of the probe in various positions that optimize probe operation. For example, it may be desirable to orient the probe horizontally (i.e., parallel to the ground surface), vertically (i.e., perpendicular to the ground surface), or at some orientation between those two positions as suits a particular probe design and/or subsurface profile. Generally speaking, a smaller overall profile of the probe results in a greater likelihood that the probe will remain undisturbed in mediums such as soil. Sensors must remain undisturbed to maintain contact with their surroundings to ensure accuracy and repeatability. Probes that are integrally formed with wireless transmitters have a much larger footprint and are readily disturbed by such things as tractors and/or foot traffic which leads to dead air spaces between the soil and probe. Air around the probes will show a lesser reading of capacitance resulting in over watering.

Sensor Assembly

Figure 2:
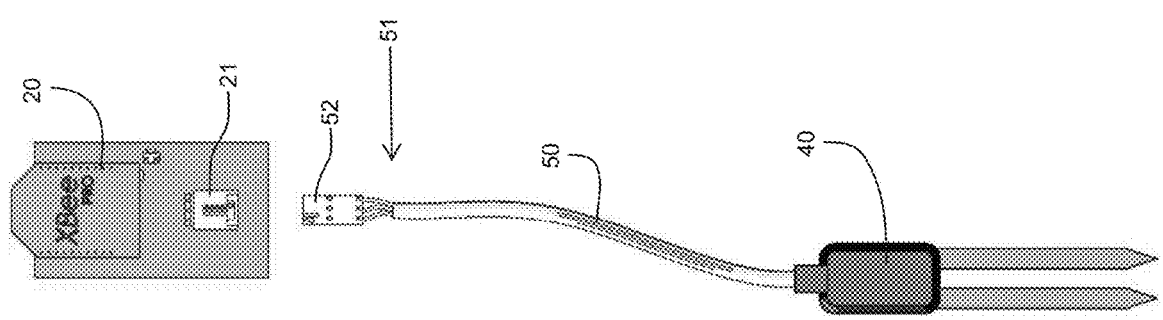
FIG. 2 is a front view of a probe disconnected from the transmitter shown in FIG. 1.
Figure 3:
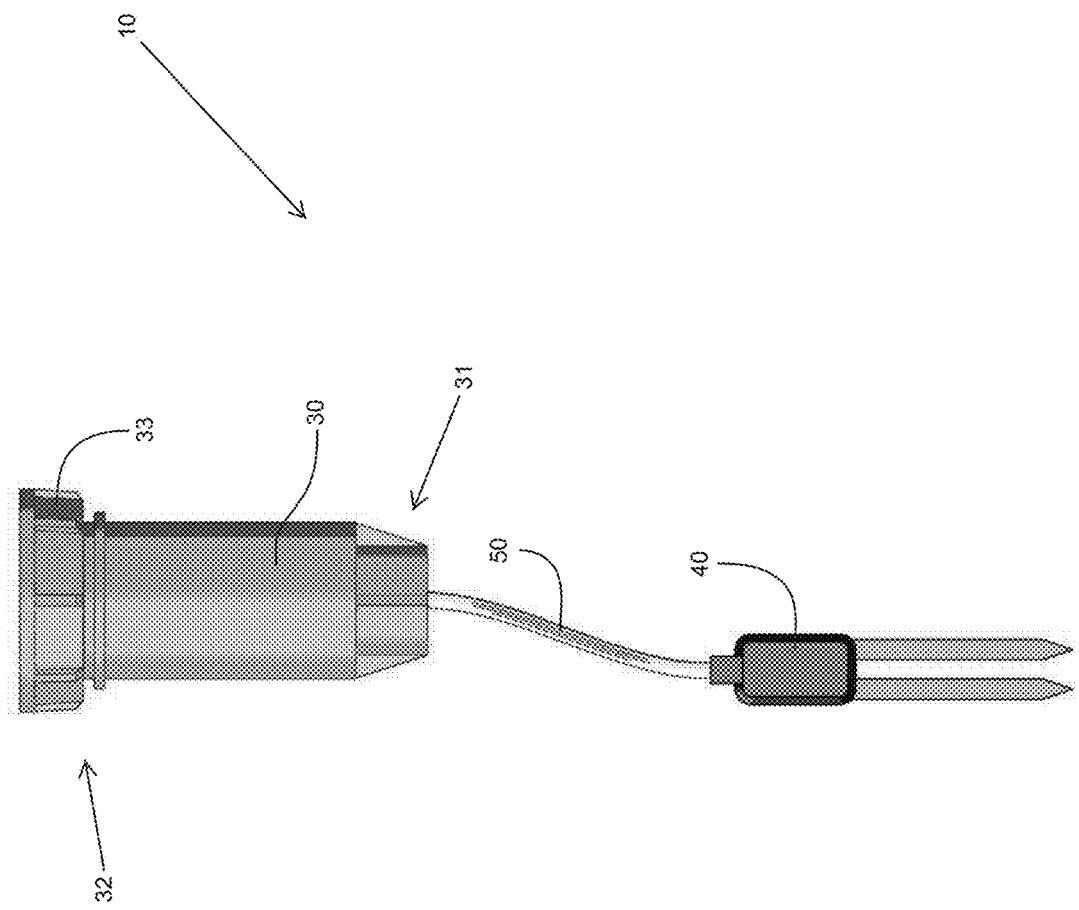
FIG. 3 is a front view of the technology shown in FIG. 2 in accordance with one aspect of the technology.

With specific reference to FIGS. 1-3, in accordance with one aspect of the technology, a probe (i.e., a sensor) and transmitter assembly 10 is disclosed having a wireless transmitter 20 disposed within a housing 30. The transmitter 20 is coupled to a probe or sensor 40 by way of a cable assembly 50. While specific reference is made herein to a wireless transmitter 20 which is powered by batteries, it is understood that a wired transmitter is also contemplated for use with the present technology. In one aspect, the transmitter 20 is an electronic device which, with the aid of an antenna, generates a radio frequency alternating current, which is applied to the antenna. When excited by this alternating current, the antenna radiates radio waves. In one aspect of the technology, the transmitter 20 is configured to communicate with an irrigation control unit (remote from the transmitter 20 and probe 40) for control of irrigation systems. In one aspect, the antenna may be enclosed inside the housing 30 or attached to the outside of the transmitter 20.

The transmitter 20 is configured to collect information from the probe 40 at a predetermined interval and transmit the data to a central receiver also at a predetermined interval. In one aspect of the technology, the transmitter 20 can be a separate piece of electronic equipment, or an electrical circuit within another electronic device such as a transceiver. In this manner, the assembly 10 may transmit information from the probe 40 at predetermined intervals and may also receive instructions from a central control unit to send information at intervals identified by the central control unit. For example, if the central control unit has failed to receive a transmission at the predetermined interval, it may send a request to the assembly 10 for information. A failure to receive a response may indicate a failed transmitter 20, failed probe 40, lack of power, or any combination thereof.

In one aspect of the invention, the cable assembly 50 comprises a three-core electrical wire system coupled to the probe 40. A proximal end 51 of the cable system 50 is coupled to an electrical connector 52. The electrical connector 52 comprises any one of a number of connectors known in the art for data communication and is configured for insertion into the receptacle 21 disposed on the wireless transmitter 20. Once inserted within the receptacle 21, the wireless transmitter 20 is in communication with the probe 40. The connector/receptacle assembly permits the use of a single transmitter design with a probe 40 of varying cable lengths as noted herein. Other types of cabling systems may be used herein as suits a particular purpose so long as the probe 40 is capable of being positioned at numerous different distances away from the transmitter 20 and at different orientations. In one aspect of the technology, multiple connector/receptacle assemblies are placed on a single transmitter 20. In this aspect, the transmitter 20 is configured to send a signal to a central irrigation control unit with the data measured from the different probes 40.

In one aspect of the technology, the probe 40 comprises a soil sensor configured to detect various physical, chemical, or other attributes of the surrounding soil including, but not limited to, volumetric water content, temperature, electrical conductivity, pH, and water potential. In one aspect, the probe 40 is configured measure soil characteristics through time domain reflectometry. Time-domain reflectometry or TDR is a measurement technique used to determine the characteristics of electrical lines by observing reflected waveforms. Time-domain transmissometry (TDT) is an analogous technique that measures the transmitted (rather than reflected) impulse. In another aspect of the technology, the probe 40 comprises a capacitance probe. Capacitance probes use capacitance to measure the dielectric permittivity of the soil. The volume of water in the total volume of soil most heavily influences the dielectric permittivity of the soil because the dielectric of water (80) is much greater than the other constituents of the soil (e.g., mineral soil: 4, organic matter: 4, air: 1). Thus, when the amount of water changes in the soil, the probe 40 will measure a change in capacitance (from the change in dielectric permittivity) that can be directly correlated with a change in water content. In one aspect, circuitry inside the probe 40 changes the capacitance measurement into a proportional millivolt output which is sent to the transmitter 20. In another aspect, the probe 40 consists of a sensing head at a fixed depth. The sensing head consists of an oscillator circuit, the frequency is determined by an annular electrode, fringe-effect capacitor, and the dielectric constant of the soil. In another aspect, the probe 40 comprises an electrical impedance sensor comprising a sinusoidal oscillator, a fixed impedance coaxial transmission line, and probe wires buried in the soil. The oscillator signal is propagated along the transmission line into the soil probe, and if the probe's impedance differs from that of the transmission line, a proportion of the incident signal is reflected back along the line towards the signal source.

Generally speaking, in an area about a moisture sensor, the amount of water (M) present may be represented by the equation $M=V/(S*d)$ wherein "V" is a volume of water (sometimes referred to as volumetric water content), "S" is an area of the electrode, and "d" is a distance between the electrodes. Therefore, "$S*d$" gives a volume (V) of a moisture detection region. A relationship between the amounts of water (M) and the capacitance (Cx) may be expressed by the following equation $Cx=[\in1'(water)*M+\in2'(others)*(1-M)]\times\in0*S/d$ wherein ($\in1'$) is the dielectric constant of water (=80) and ($\in2'$) is a relative dielectric constant of a material other than water. For example, when the material other than water is wood, the relative dielectric constant ($\in2'$) is 2. When the material other than water is air, the relative dielectric constant ($\in2'$) is 1. Thus, the capacitance (Cx) can be determined by the amount of water (M) in the detection region. In addition, the capacitance value (Cx) depends on the electrode size.

In one aspect of the technology, the housing 30 approximates the shape of a subsurface sprinkler. The wireless transmitter 20 is disposed within the interior of the housing 30. The cable system 50 extends out a bottom 31 of the housing 30 and is secured to the housing 30 with a compression fitting disposed at the bottom 31 of housing 30. The top 32 of housing 30 comprises a threaded cap 33 covering the housing 30. In one aspect, the housing 30 is water tight to minimize the intrusion of moisture into the housing 30. In one aspect, a transmitter box is located in a central location to a plurality of different transmitter and probe assemblies that are located in one or more irrigation zones. The transmitter box houses a plurality of wireless transmitters with tethered probes extending outward from the central transmitter box.

In accordance with one aspect of the technology, the moisture probe is used in connection with irrigation control. Irrigation systems utilize a moisture sensor placed in the ground that outputs information about a moisture level of surrounding soil to an irrigation controller in a separate location. The irrigation controller is coupled to and controls multiple valves that control water flow to one or more sprinkler devices. The irrigation controller processes the information received from the sensor and modifies a watering cycle for one or more valves based upon the moisture sensor measurements. In many irrigation systems, the controller uses a single moisture sensor for all of the zones (a zone is generally defined herein as an area watered by a given valve) within the irrigation system. This is a problem when, for example, different zones have different soil types or are exposed to a different amount of sunlight, traffic, or weather conditions than the soil in which the moisture sensor is located. Multiple moisture sensors may be used with the current technology and housed in a single location with the technology described herein.

In one aspect of the technology, the wireless transmitter 20 is capable of receiving simple operational parameters wirelessly from a controller, which allows the controller to set reporting intervals, selection of adaptive algorithms, etc. The wireless transmitter 20 is able to detect low battery status, to prevent the wireless transmitter 20 from failing suddenly with no warning or begin to operate intermittently reflecting battery temperature and other variability as well as possibly giving corrupted data that may result in incorrect irrigation decisions. The probe 40 and/or transmitter 20 comprises firmware that is capable of executing and reading I2C commands. An analog sensor requires I2C commands to control the oscillator and make A/D measurements. I2C commands are executed sequentially according to a sloppy timing of about +/−3 mS over 100 mS. Generally speaking, I2C can operate anywhere from 20 to 200 KHz. In one aspect of the technology, the sensor/probe firmware is able to perform simple calculations like conversion of raw A/D values into soil moisture which requires simple functions-addition, subtraction, division, polynomials but no log, trig, etc. functions. The sensor/probe firmware is capable of going into a very low power mode between set measurement intervals with routines to wake up at the end of an interval which may range from 1-100 minutes. This is set in a non-volatile configuration file which can be modified by a user. After measurement is complete, raw voltage data (or calculated soil moisture data) is to be sent to the irrigation controller. In one aspect, the sensor/probe firmware has a static soil moisture mode. This is an operational mode that allows the probe 40 to wake up, measure soil moisture, and if a change in soil moisture from the last wirelessly reported measurement does not exceed a settable threshold, return to a sleep mode without sending data. This threshold value, as well as whether this feature is enabled, can reside in a non-volatile configuration file which can be modified by a user. In one aspect, it can reside in the probe firmware or within the irrigation control unit firmware and/or software. The transmitter/probe assembly has a default mode firmware upon power restart, which allows the transmitter/probe assembly to be commissioned, i.e., assigned to a specific irrigation zone. In one aspect of the technology, the wireless transmitter/probe assembly is capable of a listening mode in a power efficient manner for receiving changes to the configuration file wirelessly from the irrigation controller and also has the ability to download full operating firmware.

Figure 4:
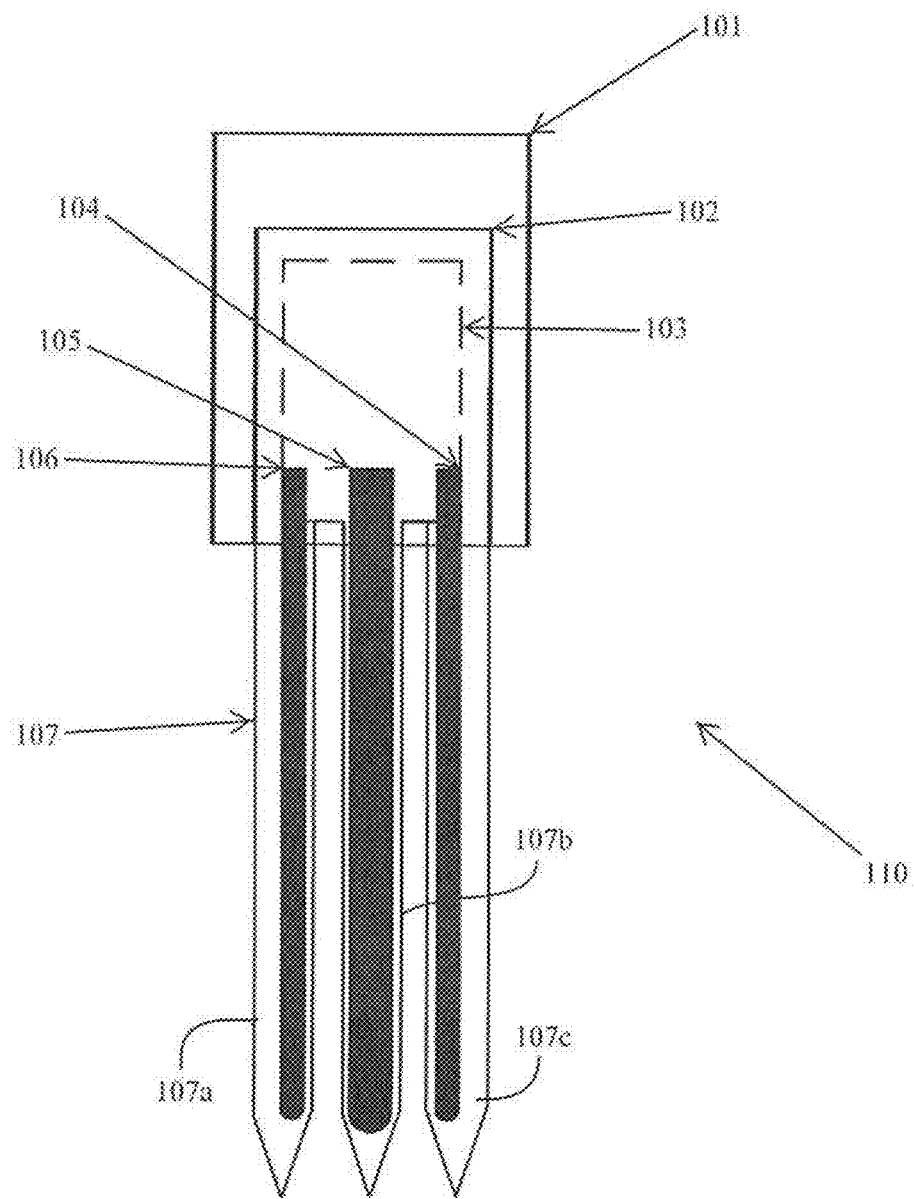
FIG. 4 is a front view of a probe in accordance with one aspect of the technology.

With reference generally to FIG. 4, in accordance with one aspect of the technology, a soil moisture probe is disclosed that measures the capacitance in the soil in which the probe is placed and by virtue of the relationship discussed above, the amount of moisture in the soil. Generally speaking, a capacitance is created between conductive traces 104 and 106 located inside the inner layers of a printed circuit board 102 in prongs 107a and 107b. The printed circuit board 102 comprises a plurality of prongs 107 that extend downward from a head 101. The head 101 includes an electronic circuit 103 comprising a capacitive to digital signal converter that measures the capacitance in the soil. The measured capacitance is proportional to the moisture in the soil surrounding the prongs 107 as noted above. In this aspect of the technology, the sensitivity of the circuit 103 is such that it is susceptible to electromagnetic interference. That is, the circuit 103 is configured to sense very small amounts of capacitance. This in turn relates to the circuit's 103 ability to detect small changes in soil moisture over a large field of influence. Because the electrical circuit 103 is sensitive to small changes in current, resistance, capacitance, etc. it may also be affected by other stray electromagnetic sources. For example, it will be influenced by electrical noise from other electronic devices in the vicinity. These sources can be RF, capacitive or inductive in nature. The electrical noise induces an equivalent electrical signal into the circuit 103 which can skew the capacitance reading. In one aspect of the technology, electrical noise is induced into the cable run from the device to a RF transmitter and/or directly, capacitively, or inductively coupled to the traces of the circuit 103. The external ground trace negates these undesirable effects by conducting them to ground effectively shorting the unwanted signal before it can affect the normal operation of the circuit 103. That is, the interference is negated by the addition of a conductive material 105 (or ground trace) separate from the circuit 103 that is in direct electrical contact with the soil. The capacitance detection traces 104 and 106 as well as all the electronic circuit 103 are isolated from contact with the soil by being encapsulated within the inner layers of the printed circuit board 102 or an encapsulating material disposed about the head 101 and around the electrical components. The ground trace 105 is disposed on an outer surface of the middle prong 107b and is gold plated to avoid corrosion when in prolonged contact with the soil. In one aspect, the detection traces 104, 106 are approximately 1.5 mm to 3 mm wide while the ground trace 105 is approximately 3 to 6 mm wide. In accordance with one aspect, the traces 104, 106 are each approximately 50 to 60 mm in length. The prongs of the probe range from approximately 60 to 70 mm in length and range from 5 mm to 10 mm in width. While specific lengths and widths are provided herein, it is understood that numerous different combinations of widths and lengths are contemplated herein. For example, the width of the individual prongs may range from 15 to 20 mm in width and 80 to 120 mm in length. In an additional non-limiting example, the ground trace 105 does not extend down a middle prong 107b. Rather, the middle prong 107b is removed and the ground trace 105 exists as a smaller grounding element nearer to the head 101.

In accordance with one aspect of the technology, the PCB is made of a corrosion resistant and ultra-violet light resistant material such as fiber glass, polyurethane, ABS or similar. The PCB is formed into a flat and thin sheet to allow easy insertion into the soil. Additional rib structures act as stiffeners and can be formed as part of the PCB to prevent twisting and bending during the insertion process. The traces 104, 105, and 106 comprise corrosive resistant metals such as gold or platinum, however due to the cost of such metals, other materials such as copper, bronze, zinc, nickel or similar can be used. Additionally conductive resins can be used in place of the metals.

In accordance with one aspect of the technology, an electrical field path of the sensor is created when an alternating electric potential is applied between the traces 104, 106. The first trace 104 and second trace 106 are formed such that the majority of the electrical field path travels perpendicular to the expose face of the traces 104, 106 and not parallel to the expose face. This can be achieved by ensuring that the first trace 104 and second trace 106 are formed such that they are thinner than they are wide. To protect the first trace 104 and second trace 106, a protective layer comprising a corrosion resistant and abrasive resistant material is attached to the PCB over the first 104 and second 106 traces. The protective layer should have a low dielectric constant relative to water to reduce its effect on the overall capacitance of the sensor. Suitable materials include fluoropolymers, chloropolymers, chlorofluoropolymers, polyparaxylene or similar materials. In operation, the sensor is inserted into the soil. The first trace 104 and second trace 106 form two plates of a capacitor with the soil immediately surrounding the traces 104, 106 forming the dielectric. Suitable measuring equipment is attached and provides a reading of the capacitance of the capacitor so formed. Since the geometry and composition of the traces 104, 106 are fixed at manufacture, changes in capacitance of the sensor is due to changes in the dielectric material or in this case the soil, hence a direct relationship between capacitance of the sensor and the wetness of the soil. The electronic circuit 103 capacitance measurement is done by measuring discharge times of RC-networks. The measurements are ratiometric. This means the capacitors are compared to a fixed reference or, like in differential sensors, to capacitors with change in opposite direction.

Due to the short time intervals and compensation methods, the ratio of discharge times is directly proportional to the ratio of capacitors. The discharge time is defined by the capacitor and the selected discharge resistor. In accordance with one aspect of the technology, the circuit 103 comprises two sets of integrated discharge resistors. One resistor set (10 k, 30 k, 90 k, 180 k, 1000 k) is for measurements on ports PC0 to PC3 and the internal reference ports PC8 and PC9. The other resistor set (10 k, 30 k, 90 k, 180 k) is for ports PC4 to PC7. This way, it is possible to measure different sensors with strongly deviated capacitance with the same chip. In accordance with one aspect of the technology, in a first step, the capacitor is charged up via a series resistor to a level close to Vdd. The resistor reduces the charge current and reduces the mechanical stress on the sensing capacitor. In a second step, the capacitor is charged up finally to Vdd without a series resistor. Then, in the third step, the capacitor is discharged via the discharge resistor down to 0V. The circuit measures the time interval until a trigger level is reached. All three of these steps are referred to as a single cycle, though it is understood that not all of the steps may be included in a single cycle and/or the order of the steps may be modified as suits a particular purpose. A sequence is made of a set of cycles, namely those for the various active ports as well as combinations of them as given by the compensation measurements. The number and kind of single cycles depends on the way of connecting the sensors, the number of capacitors and the selected compensation options. For grounded sensors, the sequence starts always with PC0 (the reference port) and then one or more of the other ports on the circuit 103. Normally, internal compensation is activated. As such the sequence ends with the measurement of the internal stray capacitance/delays. For compensating internal parasitic capacitance and the comparator delay the circuit 103 measures the discharge time with all ports being off. For compensating parallel resistances to the capacitors, the circuit 103 measures the discharge time for each capacitor a second time.

In accordance with one aspect of the technology, a 48-Bit digital signal processor (DSP) in Harvard architecture has been integrated to the circuit 103. The DSP takes the information from the capacitance to digital converter (CDC) and resolver to digital circuit (RDC) measuring units, for processing the data and makes them available to a user interface. Both the CDC/RDC raw data as well as the data processed by the DSP are stored in the RAM. The program for the DSP is stored either in the OTP or the SRAM. The DSP can collect various status information from a set of 64 I/O Bits and write back 16 of those. In this manner, the DSP can react on and also control the general purpose input-output (GPIO) pins of the circuit 103. In accordance with one aspect, the DSP is internally clocked at approximately 100 MHz. The internal clock is stopped through a firmware command, to save power. The DSP can also be clocked by other sources (e.g., a low power clock). The DSP starts again upon a GPIO signal or an "end of measurement" condition.

Figure 6:
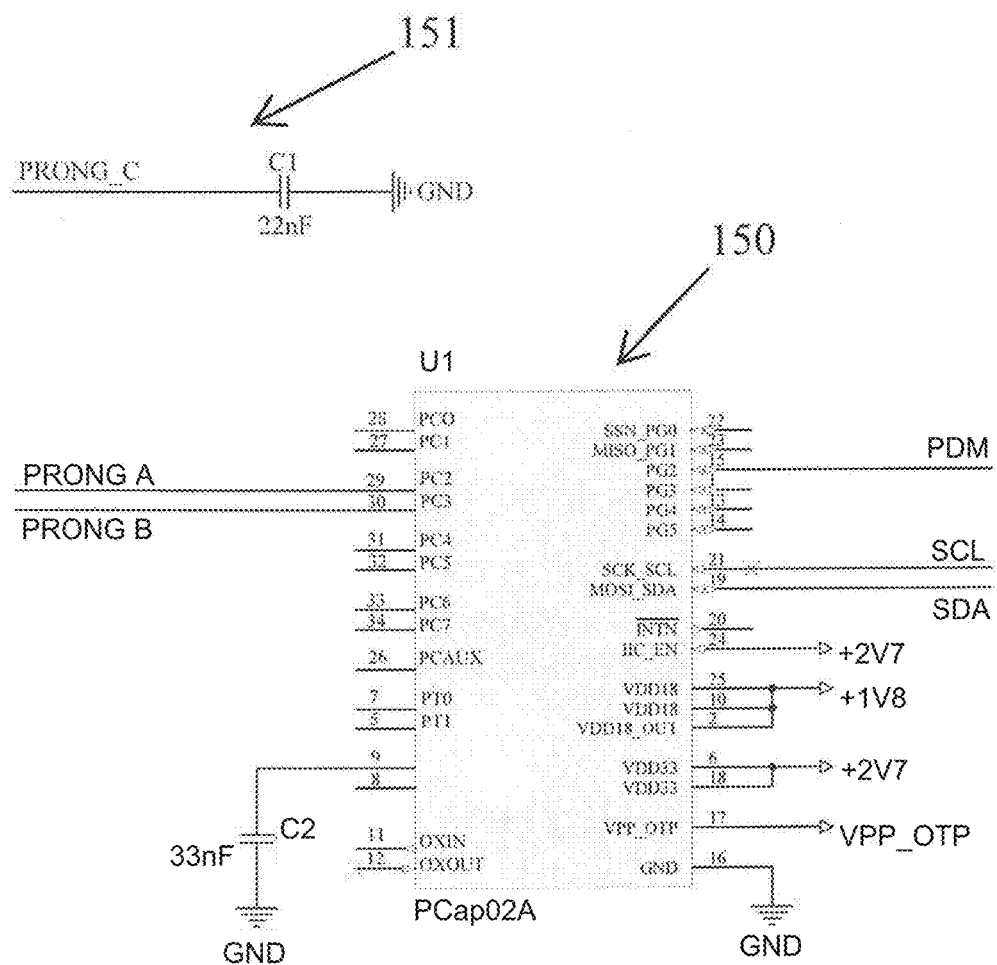
FIG. 6 is a schematic of certain probe circuitry in accordance with one aspect of the technology.

With reference now to FIGS. 5-7, in accordance with one aspect of the technology, a schematic of the circuit 103 is disclosed. The GPIO for the CDC is disclosed generally at 150 with an illustration of the connection of prong 107b shown at 151. A schematic of the sensor debug connector is disclosed at 150 and a cable connection schematic is shown at 165. A schematic showing the reverse polarity protection is disclosed at 170. A LDO regulator is disclosed at 175. A low-dropout or LDO regulator is a DC linear voltage regulator which can regulate the output voltage when the supply voltage is very close to the output voltage. A PDM filter and output buffer is shown at 180. Pulse-density modulation, or PDM, is a form of modulation used to represent an analog signal with digital data. In a PDM signal, specific amplitude values are not encoded into code words of pulses of different weight as they would be in pulse-code modulation (PCM). Instead, it is the relative density of the pulses that corresponds to the analog signal's amplitude. The output of a 1-bit DAC is the same as the PDM encoding of the signal.

Figure 8:
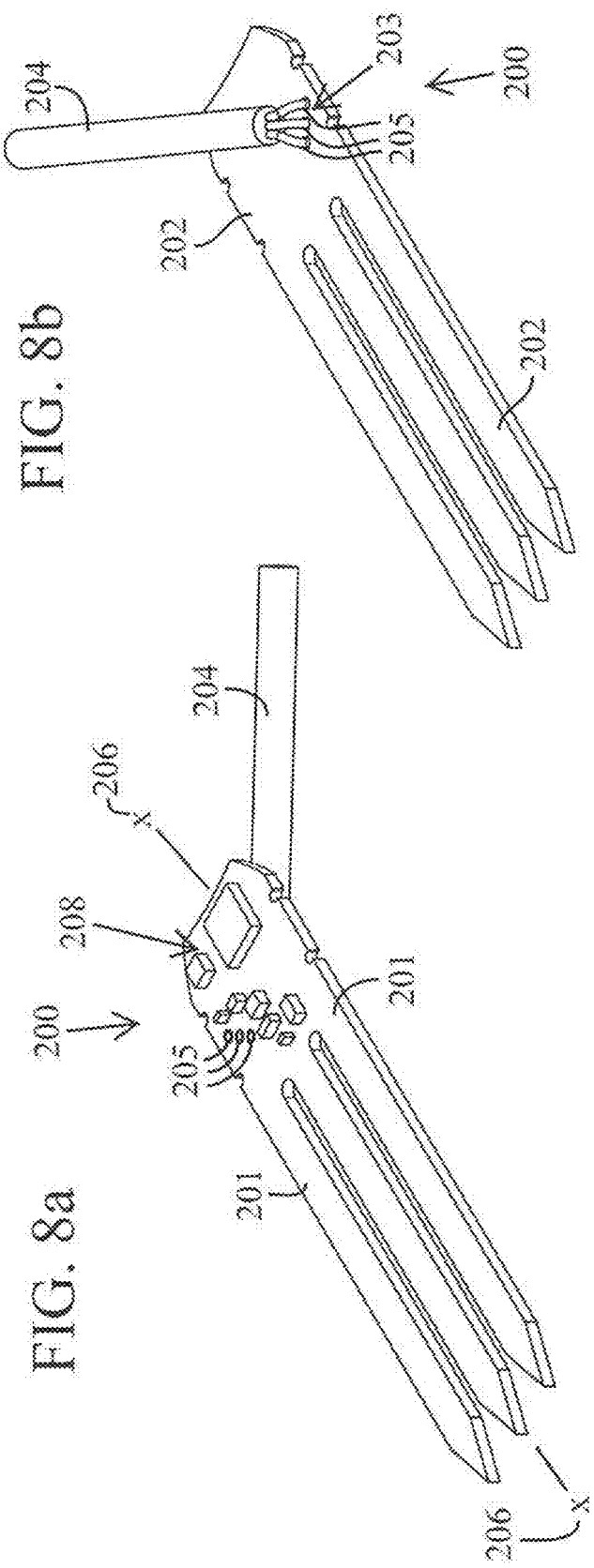

With reference now to FIGS. 8a and 8b, in accordance with one aspect of the technology, a probe 200 is disclosed having three prongs similar to that shown in FIG. 4 formed from a PCB. A front side 201 of the probe 200 comprises probe circuitry 208. A back side 202 of the probe 200 comprises a power/data connection 203 in the form of a cable 204 that is directed to a wireless transmitter or wired to a data logger as suits a particular application. A plurality of holes 205 are placed through the back side 202 of the PCB at an angle that is offset from a longitudinal axis 206 of the probe 200. In this manner, when the cable 204 is mounted to the probe 200 the natural disposition of the cable 204 is at an angle with respect to the longitudinal axis 206 of the probe 200. Advantageously, the probe 200 may be placed at an angle within the soil while the effective direction of the cable 204 with respect to a surface of the soil is either parallel to the surface or perpendicular to the surface. In the instance where the cable 204 is placed parallel to the surface, the cable 204 may be buried in the soil without additional bending of the cable 204 near its connection point on the PCB. In the instance where the cable 204 is placed perpendicular to the soil surface, the cable 204 may extend upward without bending the cable 204 near its connection point on the PCB.

Figure 9:
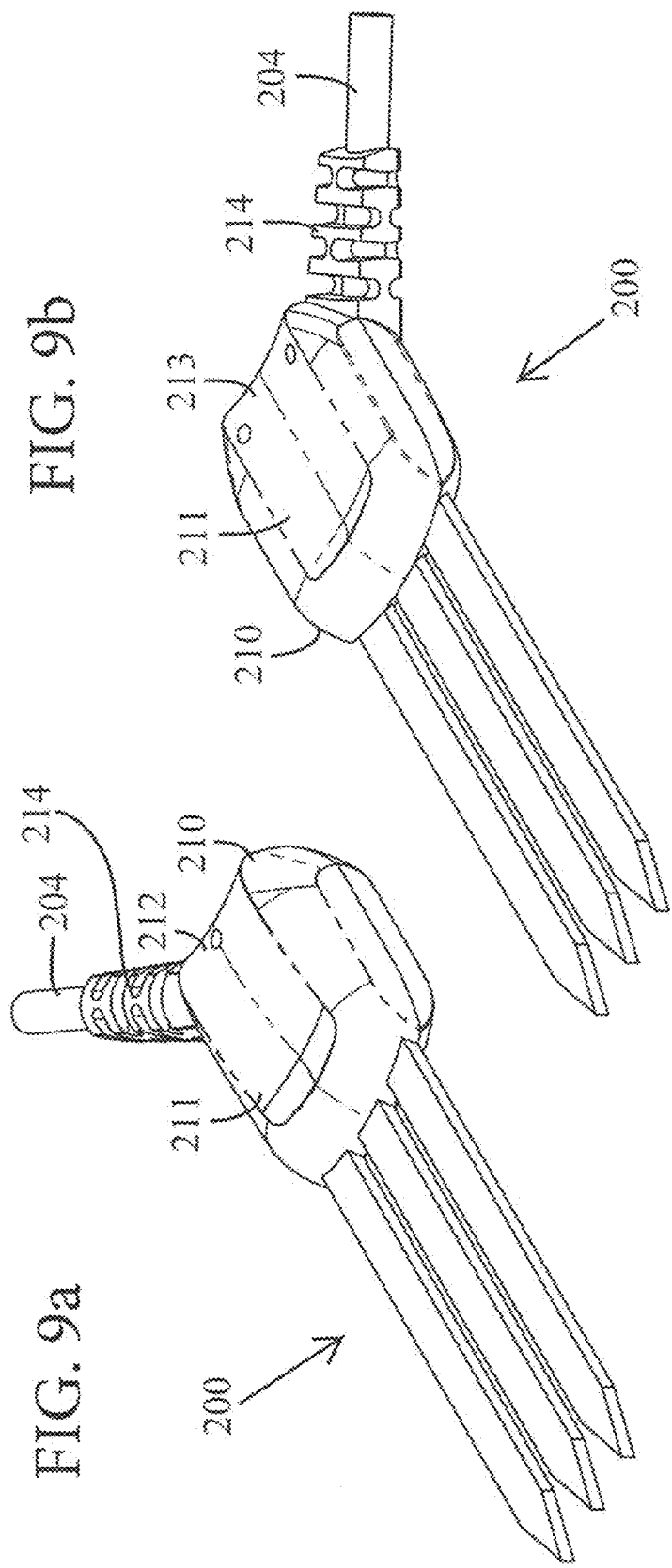
FIG. 9a is a top perspective view of one side of a probe in accordance with one aspect of the technology.
FIG. 9b is a bottom perspective view of the probe shown in 9b.

With reference now to FIGS. 9a and 9b, in accordance with one aspect of the technology, the circuitry 209 of probe 200 is encased in an overmold 210 that leaves the prongs exposed for sensing within the soil. The overmold 210 is watertight to prevent the incursion of liquid into the probe circuitry 209 and comprises a tapered channel 211 on the front 212 and back 213 of the overmold 210. The tapered channel 211 accommodates the user's thumb and forefinger, for example, for easier placement of the probe 200 into the soil. In addition, the overmold 210 includes a cable overmold component 214. The cable overmold 214 increases the surface area of the entire overmold 210 that may be held within the hand of the user. With the cable 204 disposed at an angle with respect to the longitudinal axis 206 of the probe 200, the entire overmold 210 is easier to handle.

Figure 10:
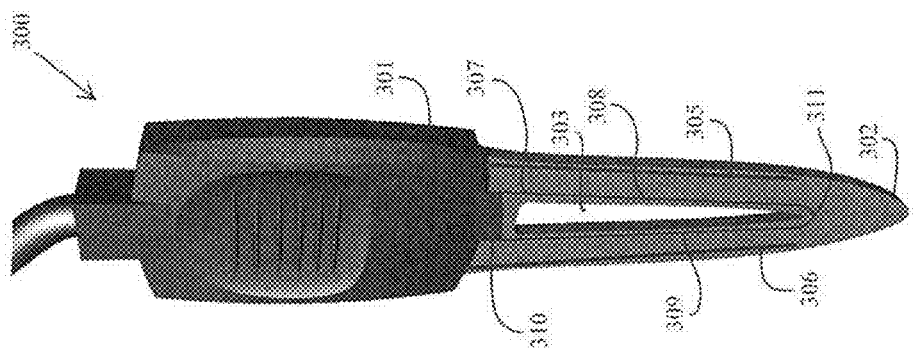
FIG. 10 is a perspective view of a probe in accordance with one aspect of the technology.

With reference now to FIG. 10, in accordance with one aspect of the technology, a probe 300 is shown having a head 301 the encloses circuitry similar to that described herein. The circuitry is coupled to a PCB with a distal end 302 that has a general V-shape to enable easier insertion into the soil. In one aspect, an aperture 303 is disposed between opposing sides of the V-shaped distal end 302. Embedded within the PCB are traces 305 and 306 which act to measure the capacitance as discussed herein. A ground trace 307 is also embedded within the PCB and coupled to the circuitry. The ground trace 307 is disposed about opposing sides of the aperture 303 with a first prong 308 and second prong 309 connecting at a top 310 and bottom 311 of the trace 307. While the PCB is coupled together at the distal end 302 of the probe 300, the capacitance traces 305 and 306 are not electrically coupled together (i.e., they are capable of independently conducting a signal exclusive of one another).

Figure 11:
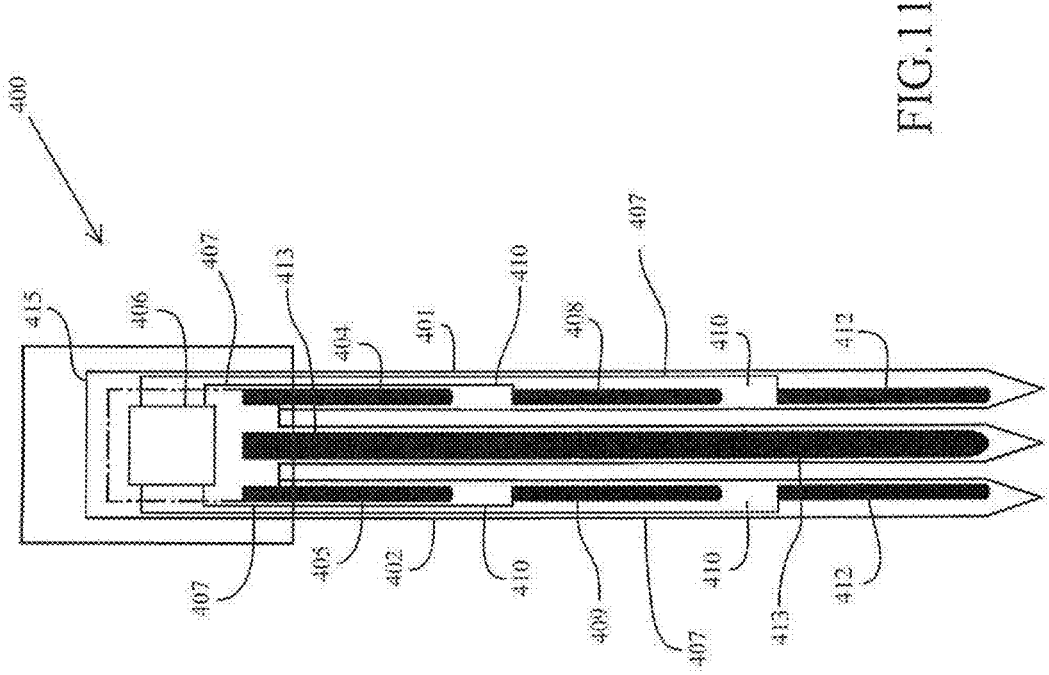
FIG. 11 is a front view of a probe in accordance with one aspect of the technology.

With reference now to FIG. 11, in accordance with one aspect of the technology, a probe 400 is disclosed. The probe 400 includes three sets of traces down prongs 401 and 402. Each prong set of traces corresponds to a different depth range and is intended to provide a more detailed or precise measurement of soil moisture along the entire depth of the probe 400. In one aspect of the technology, a first trace set comprises traces 404 and 405. The first trace set is approximately 30 mm to 50 mm in length, is disposed at the top of the prongs 401, 402 and is coupled to the prong circuitry 406 either directly or through a printed circuit line 407 manufactured in the PCB 415 as is known in the art. A second trace set comprising traces 408 and 409 is disposed about the middle of the prongs 401, 402. Each of the traces of the second trace set are likewise 30 mm to 50 mm in length. A third trace set comprising traces 411 and 412 is disposed about the bottom of the prongs 401, 402. A ground trace 413 is disposed about the entire length of the middle prong (e.g., 80 to 110 mm). Each of the second and third trace sets are electrically coupled to the probe circuitry 406 through a printed circuit line 407 manufactured into the PCB 415. While a space 410 is located between the first and second trace sets and the second and third trace sets to minimize potential interference, different aspects of the technology do not require that a space be present. In one aspect, the space 410 is calculated to be between 20 and 30 percent of the total length of each trace. For example, if trace 404 is 30 mm, the space between trace 404 and 409 would be between 6 and 9 mm. In some aspects of the technology, the top and bottom of adjacent trace sets are within 1 mm of each other or spatially overlap one another. That is, the bottom of one trace is over the top of a vertically adjacent trace. In the instance where the traces spatially overlap, an insulating layer is disposed between the traces so that they are not electrically conductive with one another. While a probe with three trace sets is shown in FIG. 11, a probe with only two trace sets may be used or a probe with more than three trace sets may be used as suits a particular application. Moreover, the trace sets may be longer or shorter than the examples provided in this paragraph and the total probe length may be longer or shorter than the example provided depending on the application.

In accordance with one aspect of the technology, a signal is sent to each of the detection trace sets simultaneously and the capacitance measurements from each of the trace sets is combined to determine an average soil moisture over the entire length of the prong. Individual soil moisture measurements in each zone are necessarily calculated and may also be reported as suits a particular application. In another aspect of the technology, a signal is sent sequentially (i.e., cycled) to each of the different trace sets to minimize potential interference between active capacitance measurements. That is, at time n a signal is sent to the first trace set and a first capacitance is measured. At time n+1 (e.g., 1 millisecond, 2 milliseconds, or 3 milliseconds), a signal is sent to the second trace set and a second capacitance is measured. At time n+2, a signal is sent to the third trace set and a third capacitance is measured. This process can be repeated numerous times to achieve a satisfactory measurement of capacitance at the different levels. Advantageously, the staggered trace lines of probe 400 provide for a more precise measurement of soil moisture over the entire length of the probe. In this manner, watering schedules may be tailored to ensure that water is delivered to a specific depth before the water is turned off. It can also provide historical information with respect to the wetting profile in a particular soil zone which will provide water managers with important data regarding water usage rates and fine tuning of water schedules. For example, in an instance where a moisture sensor determines that the moisture content in the root zone of a particular plant has reached an optimum level, a signal is sent to the irrigation control box and water is shut off to that zone. However, based on a particular wetting profile, this may result in over-watering as excess water above the root zone may trickle down into the root zone. Knowledge of the historical wetting profile allows water managers to terminate watering before the root zone is saturated, knowing that a particular soil moisture content above the root zone will result in an appropriate amount of moisture within the root zone after a period of time has elapsed. In accordance with one aspect of the technology, a known quantity of capacitive interference is subtracted from the capacitive measurements in each one of the trace sets resulting from the interference created by adjacent trace sets.

Irrigation Control System

In one aspect of the technology, the system utilizes a moisture probe (including, but not limited to, those probes/sensors described above) in connection with irrigation control systems. Irrigation systems utilize a moisture sensor/probe placed in the ground that outputs information about a moisture level of surrounding soil to an irrigation controller in a separate location. The irrigation controller is coupled to and controls multiple valves that control water flow to one or more water delivery devices. The irrigation controller processes the information received from the sensor and modifies (initiates or terminates) a watering cycle for one or more valves based upon the moisture sensor measurements. In many irrigation systems, the controller uses a single moisture sensor for all of the zones (a zone generally defined as an area watered by a given valve) within the irrigation system. This is a problem when, for example, different zones have different soil types or are exposed to a different amount of sunlight, traffic, or weather conditions than the soil in which the moisture sensor is located or different zones have different types of watering needs based on watering technique (e.g., drip system vs. above-ground sprinklers) or different plant types (e.g., cherry trees vs. alfalfa). Multiple moisture sensors may be used using the current technology and housed in a single location with the technology described herein to control the watering rates.

In accordance with one aspect of the technology, irrigation cycles are controlled based on the different measurements of soil moisture taken in different water zones. Measuring soil moisture at varied depths in a given soil profile provides information to the water manager regarding adjustment of irrigation control during an ambient temperature increase or decrease, for example. Grasses and other plants with shallow root systems (for example, the top 12") draw water from shallower depths during higher temperatures such as above 80 degrees F. and deeper root structure below 80 degrees F. Higher ambient temperatures require less water per application (shorter duration) with more frequent irrigation events to maintain Plant Available Water (PAW) at the upper range of the finer root structures. Lower ambient temperatures cause plants to use the larger diameter, deeper root structure requiring more water per application (longer duration) with less frequency to maintain but not surpass PAW. In addition, the dielectric permittivity of water decreases as the temperature measured in the soil decreases. A decrease in the dielectric permittivity results in a decrease in the measured soil moisture. Accordingly, a decreased temperature in the soil/water measured in the area of the probe can result in a false negative resulting in overwatering.

In accordance with one aspect of the technology, a temperature measurement is taken by a temperature sensor element placed in the moisture sensor and located in the vicinity of each capacitance detection trace. The temperature data is transmitted to an irrigation control unit and is utilized to "scale down" the amount of moisture detected by a soil moisture probe required to terminate a watering event. In one non-limiting example, in an instance where the temperature taken near the soil moisture probe indicates that the soil moisture is 5 percent lower than a direct gravimetric measurement of free soil moisture, the irrigation control unit automatically adjusts the threshold soil moisture measurement required to automatically terminate a water event by 5 percent. That is, if a threshold soil moisture value required to terminate a watering event is 35 percent VWC, and the temperature at the probe indicates a 5 percent "false negative" then the threshold soil moisture value required to terminate a watering event is automatically adjusted to 30 percent to account for the change in probe operation. In an additional aspect, an ambient outside air temperature is also taken at the transmitter housing (or other location representative of temperature near an area relevant to plant growth) and is used by water managers to adjust watering schedules to accommodate the zone at which roots will remove water from the soil profile. That is, the irrigation controller can be set to ensure that water is available at the root zone where the plant is most likely to uptake water based on the ambient temperature and the temperature of the soil. In one non-limiting example, where the ambient air temperature is measured at 90 degrees F., the irrigation controller is programmed to selectively read soil moisture measurements taken from probes that detect soil moisture from zero to 12 inches below the soil surface. Likewise, in an example where the ambient air temperature is measured at 70 degrees F., the irrigation controller is programmed to selectively read soil moisture measurements taken from probes that detect soil moisture at depths greater than 12 inches below the soil surface. Water terminating or initiating events are therefore based on soil moisture values taken from a specific zone that corresponds to a specific temperature regime and corresponding water uptake characteristics of the plant matter. While not restricted to subsurface drip irrigation systems, the modification of water schedules based on instantaneous temperature measurements is believed to be most effective with a system that can deliver water to a specific root zone more quickly such as with a drip irrigation system. However, surface irrigation systems can also be used in connection with this method. In certain aspects, the length of the moisture probe is varied to accommodate different root structures and/or multiple moisture probes positioned at different depths are used. Moreover, water application monitoring and control or depletion of PAW can be utilized slightly before harvest of many plants/vegetables to stress the plant to aid in the separation of vine and fruit.

Figure 12:
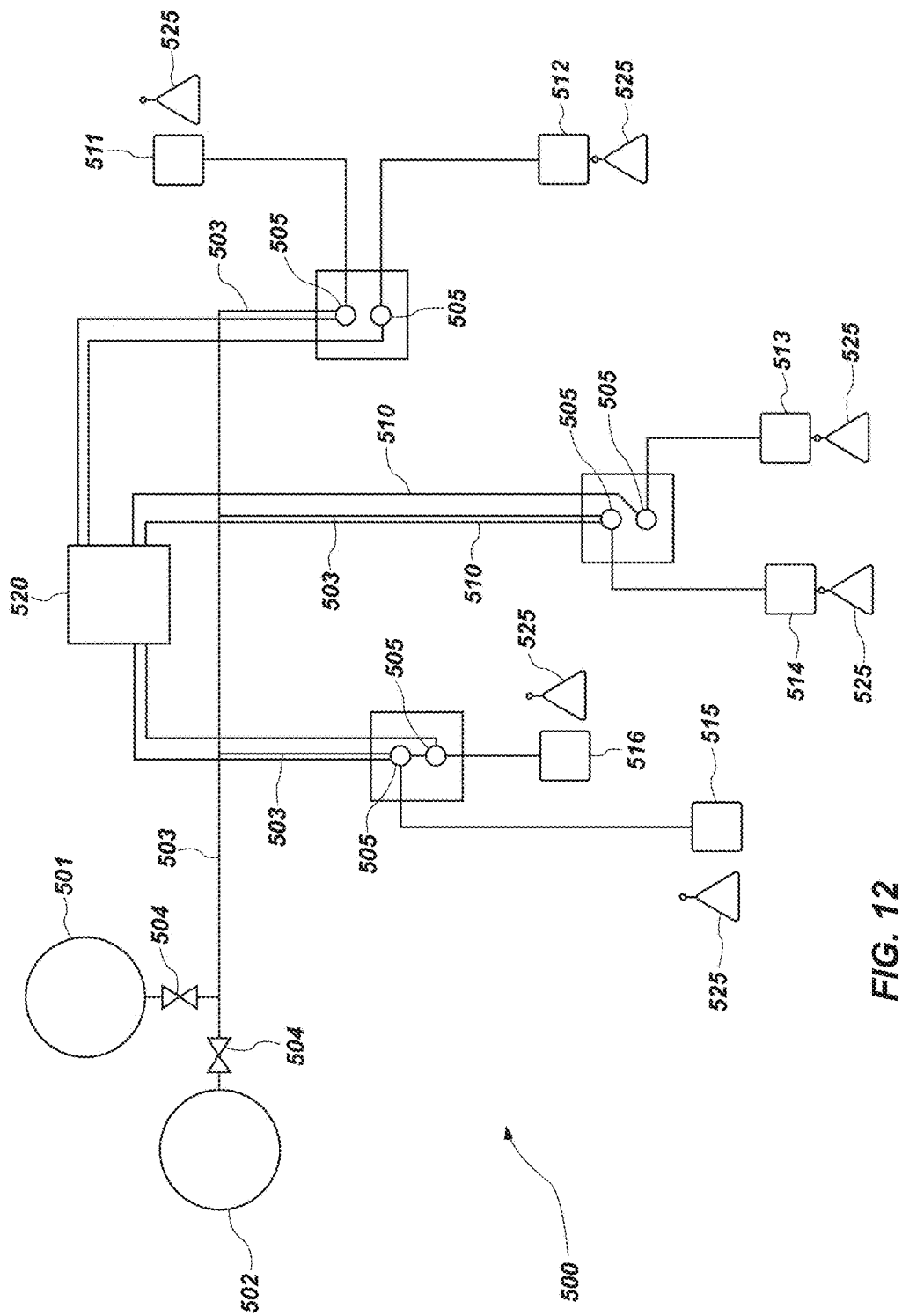
FIG. 12 is a diagram of an irrigation control system in accordance with one aspect of the technology.

With reference now to FIG. 12, in accordance with one aspect of the technology, a hierarchy of watering cycles and a method of managing water demands is disclosed. In one aspect of the technology, an irrigation control system 500 is shown generally. The system comprises one or more water sources 501, 502 coupled to a plurality of irrigation valves 505 by way of a conduit 503, wherein the valves 505 are disposed in an irrigation box 506. Each of the valves 505 provides water to one or more water dispensers divided into zones. The zones represent different geographic locations and/or a combination of different water applications (i.e., drip irrigation, sprinkler irrigation, subsurface drip, etc.) at the same geography. While more or less zones may be used in any particular application, six zones are shown on FIG. 12 as 511, 512, 513, 514, 515, and 516, respectively. The valve 505 associated with each zone is coupled to an irrigation control unit 520 by power lines 510. The irrigation control unit 520 provides water managers with a tool to turn on or turn off water to a particular zone at will. At least one wireless transmitter/moisture probe assembly 525 is disposed within each zone. While a single assembly 525 is shown in each zone, it is understood that more than one transmitter/probe assembly 525 can be used in a single zone. In one aspect of the technology, the assembly 525 is configured to detect a capacitance value in the area of influence of the probe and transmit the capacitance value to the irrigation control unit 520. The control unit 520 is equipped with a receiver and processor that receives the raw capacitance value from the transmitter assembly 525 and converts that value into a soil moisture value. However, in one aspect, the transmitter 525 is equipped with a processor that converts the raw capacitance value into a soil moisture value before transmitting the data to the control unit 520. In one aspect of the technology, the irrigation control unit 520 regulates water flow by turning on valves 505 when a predetermined low threshold of soil moisture is detected and turning off the valves 505 when a predetermined high threshold of soil moisture is detected. In this manner, more consistent PAW is maintained which keeps nutrients and fertilizers at the root zone instead of draining into the groundwater. This allows plants to use water during the heat of the day when the most water is needed. Water is conserved by not maintaining a reservoir at night for use during the day. In one aspect of the technology, a soil moisture value ranging from approximately 20 percent VWC to 40 percent VWC is set as the upper or high threshold value whereas the lower threshold value ranges from approximately 10 percent VWC to 35 percent VWC. One of ordinary skill in the art will appreciate that these values may change significantly based on the type of plant matter (soy beans, onions, alfalfa, etc.), soil type, geography, temperature, and the like. For example, in a sandy soil the upper threshold may range from 32 percent VWC to 38 percent VWC and the lower threshold may range from 25 percent VWC to 29 percent VWC.

In accordance with one aspect of the technology, the irrigation control unit 520 is coupled to a weather control station that is configured to take measurements with respect to numerous ambient characteristics to optimize watering schedules, including rain, wind, temperature, humidity, etc. While soil moisture is expressly referenced herein, it is understood that numerous other types of measurements of soil chemistry and/or soil characteristics may be taken with a soil probe (either combined with the probe described herein or with a separate probe), including, but without limitation pH, electrical conductivity, etc. In one aspect, pH sensors are used in conjunction with an injection and drip irrigation system that utilizes chemicals to lower the pH of the water supply. Water supplies in some areas emanate from a multitude of drainages that may have substantial differences in pH. Water sources 501 and 502 are regulated by valves 505. Each valve may be selectively opened or closed to regulate the pH of the water stream entering the irrigation system. Measuring the ambient pH in any particular zone may be used to regulate which water source is used to irrigate a particular zone. For example, if zone 511 has a particularly low pH and the plant matter growing in zone 511 would benefit from an increased pH level, water from either water source 501 or 502 may be released into the irrigation system for use depending on the respective pH values of the water from those sources. This permits water managers to use lower quality water in irrigation applications that do not require higher water quality irrigation. Lowering pH can also clean hardened deposits from pipes, tubing and emitters as well as ponds and reservoirs. In one aspect, EC or "electro conductivity" sensors are used to identify salts and other soil chemistry scenarios where a flushing event may be necessary and/or where other tasks would benefit the plant matter.

In addition, temperature and humidity can be used together to calculate dew point to determine the most appropriate watering time and amount of water needed. In some aspects, temperature and humidity are used to regulate atmospheric moisture delivery/humidity control in green houses and other irrigation enclosures. In other aspects, wind speed and direction, including wind sheer, can alert and modify watering events. In one non-limiting example, the water manager may divert downwind watering duration to an upwind location in order to optimize a watering event.

In accordance with one aspect of the technology, the irrigation control unit 520 is programmed with a water delivery hierarchy. For example, in one aspect of the technology, if more than one transmitter/probe assemblies 525 sends a signal to the control unit 520 indicating that water should be delivered to more than one zone, the control unit 520 will open the valve 505 to the zone associated with the signal from the transmitter/probe assembly 525 that was first in time. After the watering event for the zone that was first in time has concluded, the watering event for the zone that was second in time is initiated and so forth. In accordance with one aspect of the technology, a system override is programmed into the control unit 520 to allow the water manager to select specific zones to have priority over other zones based on any number of factors, including the scarcity of water and the nature of the plant matter being irrigated. In one non-limiting example, a plurality of zones may include a green and two different portions of a fairway of a golf course. Because the greens of the course may be considered to be more delicate, more expensive to maintain, and/or more expensive to replace, the water manager may place a system override to deliver water to the green first even though a transmitter/sensor assembly 525 associated with the fairway may have sent a signal to the control unit 520 indicating that a water event should be initiated prior to the delivery of a signal from a transmitter/sensor assembly 525 associated with the green. In one aspect, the hierarchy override provides for a stop command to be issued to discontinue a watering event if a water demand signal emanates from a high priority zone. Other non-limiting examples include time-of-year or time-of-day irrigation demands where certain crops may be susceptible to greater harm from lack of water. For example, different crops may be present in different watering zones. A crop that has been newly planted in the spring and requires more maintenance in order to survive may be given a higher priority ranking than a crop that was planted in the fall and is more established. In another example, crops may be equally established, but one crop may simply be more susceptible to water stress and hence have priority over the other crop. Other priority considerations include soil type and the amount of water pressure available in a situation where enough water is available to provide a watering event for more than one zone. That is, due to the layout of the irrigation system, adjacent zones may both call for water, but there may be inadequate water pressure to the irrigation system design.

In one aspect of the technology, once a transmitter/sensor assembly 525 has sent a signal to the control unit 520 that a watering event is needed it shuts down for a predetermined period of time to conserve battery power. In one-non-limiting example, the shut down time is set for the minimum amount of time estimated to increase the soil moisture in the zone to above the threshold level. This requires the transmitter/sensor assembly 525 to have a receiver as well as a transmitter to enable communication with the control unit 520. In another aspect, the transmitter/sensor assembly 525 is preprogrammed with a minimum shut down time (e.g., 5 minutes, 10 minutes, or 15 minutes). The control unit 520 is programmed to provide a notice when it has not received a signal from any one transmitter/sensor assembly 525 for longer than a threshold period of time (e.g., 5 minutes, 10 minutes, or 15 minutes). In another aspect of the technology, in a scenario where multiple zones have "called" for a watering event through the signal of a transmitter/sensor assembly 525 and the priority zone has been watered, the control unit 520 is programmed to reassess the priority status of zones that have "called" for a watering event and initiate watering based on the then current priority status.

Persons skilled in the art of irrigation controllers will appreciate that the present technology also provides a method of watering turf, crops, and/or landscaping, etc. in order to conserve water. In one embodiment, the method includes the steps of providing a stand-alone irrigation controller having a plurality of manually actuable controls; entering or selecting a watering program via the manually actuable controls; selecting pre-programmed watering restrictions via the manually actuable controls that disable portions of the watering otherwise effectuated by the watering program; and watering turf, crops, and/or landscaping by having a processor in the irrigation controller turn a plurality of valves ON and OFF in accordance with the watering program as dictated by the soil moisture values and/or the hierarchy of zones that are ranked to receive water according to their rank in the hierarchy. It will be understood that the order of the steps of entering or selecting the watering program on the one hand, and selecting pre-programmed watering restrictions on the other hand, can be conducted in various different manners. While an example of a stand-alone irrigation controller with selectable watering restrictions is disclosed, a PC-based irrigation management system that implements watering restrictions, and a method of watering turf and/or landscaping to conserve water, have been described, it will be apparent to those skilled in the art that the subject invention can be further modified in arrangement and detail. For example, the stand-alone irrigation controller may include, but need not have, a modular configuration with removable station modules. The irrigation controller could be configured to operate with decoder technology instead of requiring each valve to be separately connected to a dedicated station circuit in a station module, or permanently built into the controller.

In one aspect of the technology, a plurality of irrigation controllers at different irrigation sites are managed by a personal computer (PC) running a specialized irrigation water management application program. The PC is connected via a central computer communication unit site interface. The site interface unit is connected to a flow sensor and to the irrigation controller. The PC is connected to the Internet via internal modem and phone line, cable modem, or wireless Internet connection to allow downloading of current watering restrictions from water districts and weather data (e.g., temperature, humidity, etc.) from the National Weather Service or on-site weather stations. In managing different irrigation sites through the PC, the watering program can be selected by the user via point-and-click menus. The fields for selecting the watering restrictions can be much more descriptive in the PC environment. For example, the user can select the actual name of the zone. The user can also select the water district directly or from a graphic menu. Selecting a location from a map can also impose the watering restrictions. The PC can manage watering at multiple geographically disparate sites that are subject to different watering restrictions, different plant types, soil types, etc.

The storage component contains memory for storing information used for performing the methods and operating the devices described herein. Memory refers to electronic circuitry that allows information, typically computer data, to be stored and retrieved. Memory can refer to external devices or systems, for example, disk drives or other digital media. Memory can also refer to fast semiconductor storage, for example, Random Access Memory (RAM) or various forms of Read Only Memory (ROM) that are directly connected to the processor. Computer terminals represent any type of device that can access a computer network. Devices such as PDA's (personal digital assistants), cell phones, personal computers, lap top computers, tablet computers, mobile devices, or the like could be used. The computer terminals will typically have a display device and one or more input devices. The network may include any type of electronically connected group of computers including, for instance, Internet, Intranet, Local Area Networks (LAN), or Wide Area Networks (WAN). In addition, the connectivity to the network may be, for example, remote modem or Ethernet.

As will be appreciated by one skilled in the art, aspects of the present invention may be embodied as a system, method or computer program product used in connection with an irrigation controller and/or moisture sensor and transmitter assembly. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present technology may be written in any combination of one or more programming languages, including an object oriented programming language such as Java, Visual Basic, SQL, C++ or the like and conventional procedural programming languages, such as the "C" programming language or similar programming languages. The program code may execute entirely on a user's computer, partly on the user's computer, as a stand-alone software package, partly on the user's computer and partly on a remote computer, entirely or partly within an irrigation controller or moisture sensor/transmitter assembly, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The foregoing detailed description describes the technology with reference to specific exemplary aspects. However, it will be appreciated that various modifications and changes can be made without departing from the scope of the present technology as set forth in the appended claims. The detailed description and accompanying drawings are to be regarded as merely illustrative, rather than as restrictive, and all such modifications or changes, if any, are intended to fall within the scope of the present technology as described and set forth herein.

More specifically, while illustrative exemplary aspects of the technology have been described herein, the present technology is not limited to these aspects, but includes any and all aspects having modifications, omissions, combinations (e.g., of aspects across various embodiments), adaptations and/or alterations as would be appreciated by those in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus-function are expressly recited in the description herein. Accordingly, the scope of the technology should be determined solely by the appended claims and their legal equivalents, rather than by the descriptions and examples given above.

The invention claimed is:

1. A system for controlling irrigation, comprising:
   a plurality of wireless transmitters coupled to a plurality of stand-alone soil moisture probes, wherein a single wireless transmitter is coupled to a single probe by a length of cable, and wherein each of the probes corresponds to a separate irrigation zone, said probe comprising:
first and second elongate conductive materials encapsulated in a non-conductive substrate, said first and second elongate materials coupled to a power source and configured to be placed in the soil to form a capacitor;
third and fourth elongate conductive materials encapsulated in the non-conductive substrate, said third and fourth elongate materials being conductively isolated from the first and second elongate conductive materials, coupled to a power source and configured to be placed in the soil to form a capacitor;
a soil moisture circuit encapsulated in the non-conductive substrate coupled to the power source, said circuit having an oscillator for applying an electrical stimulus to the first and second elongate conductive materials and to the third and fourth elongate materials; and
a ground conductive material in direct electrical contact with the soil disposed between the first and second elongate conductive materials, said ground conductive material being coupled to the soil moisture circuit and conductively isolated from the first and second elongate conductive materials;
wherein the non-conductive substrate comprises a printed circuit board having a head and three coplanar prongs extending downward from the head, the first and second prongs extending downward from opposing sides of the head and the third prong extending downward between the first and second prongs, and wherein the first and third conductive materials are disposed within the first prong and the second and fourth conductive materials are disposed within the second prong, and wherein the ground conductive material is disposed on an outer surface of the third prong;
an irrigation control box operatively coupled to a plurality of irrigation valves, wherein each of said irrigation valves corresponds to separate irrigation zones, and wherein said irrigation control box is configured to control the irrigation valves based on an upper and a lower soil moisture threshold value and comprises a receiver configured to receive a wireless data signal from the plurality of transmitters;
wherein the irrigation control box is configured to receive a signal corresponding to an ambient temperature within an irrigation zone, and upon detecting that the ambient air temperature exceeds a threshold level, the irrigation control box is configured to modify the upper and lower soil moisture threshold values.

2. The system of claim 1, wherein the soil moisture circuit is configured to simultaneously apply an electrical stimulus to the first, second, third, and fourth elongate conductive materials.

3. The system of claim 1, wherein the soil moisture circuit is configured to simultaneously apply an electrical stimulus to the first and second elongate conductive materials followed by a simultaneous electrical stimulus to the third and fourth elongate conductive materials after a predetermined period of time.

4. The system of claim 1, wherein the cable extends outward from a head at an angle that is non parallel with a longitudinal axis of the probe.

5. The system of claim 4, wherein the head comprises a plurality of three collinear apertures each housing a coupling to the cable, the apertures being disposed at an angle that is non parallel with the longitudinal axis of the probe.

6. The system of claim 5, wherein the head of the probe is covered in a watertight covering that covers a portion of the cable.

7. The system of claim 1, wherein the irrigation control box contains a processor programmed to:
(i) convert signal data received from the plurality of transmitters into a soil moisture value;
(ii) open an irrigation control valve corresponding to the irrigation zone to which the probe corresponds upon detecting that the soil moisture value in the irrigation zone has dropped below a threshold value; and
(iii) close the irrigation control valve corresponding to the irrigation zone to which the probe corresponds upon detecting that the soil moisture value in the irrigation zone has raised above a threshold value.

8. The system of claim 1, wherein the third elongate conductive material is disposed below the first elongate conductive material in the first prong and the fourth elongate conductive material is disposed below the second elongate conductive material in the second prong.

9. The system of claim 1, wherein the irrigation control box is configured to receive a signal corresponding to an ambient temperature within an irrigation zone, and upon detecting that the ambient air temperature exceeds a threshold level, the irrigation control box is configured to modify the upper and lower soil moisture threshold values.

10. A method of controlling irrigation, comprising:
using a plurality of probes to detect a capacitance value in soil in a plurality of irrigation zones, wherein at least one probe is located in each of the plurality of irrigation zones, and wherein each probe is tethered to a wireless transmitter configured to send a wireless signal to an irrigation control box;
transmitting a wireless signal from each of the plurality of wireless transmitters to a receiver coupled to the irrigation control box;
receiving a plurality of signals from the plurality of wireless transmitters into a processor of the irrigation control box, said plurality of signals corresponding to the capacitance value in the soil measured in each one of the plurality of irrigation zones;
converting the capacitance values to a soil moisture value and comparing the capacitance values to pre-determined upper and lower soil moisture threshold values;
upon detecting that a soil moisture value in an irrigation zone has dropped below a lower threshold value, opening an irrigation control valve corresponding to the irrigation zone having the soil moisture value below the lower threshold value;
upon detecting that a soil moisture value in an irrigation zone has raised above an upper threshold value, closing the irrigation control valve corresponding to the irrigation zone having the soil moisture value above the upper threshold value;
measuring the ambient air temperature proximate to an irrigation zone; and
upon detecting that the ambient air temperature exceeds a threshold level, modifying the upper and lower soil moisture threshold values;
wherein the probes comprise:
first and second elongate conductive materials encapsulated in a non-conductive substrate, said first and second elongate materials coupled to a power source and configured to be placed in the soil to form a capacitor;

a soil moisture circuit encapsulated in the non-conductive substrate coupled to the power source, said circuit having an oscillator for applying an electrical stimulus to the first and second elongate conductive materials;

third and fourth elongate conductive materials encapsulated in the non-conductive substrate, said third and fourth elongate materials being conductively isolated from the first and second elongate conductive materials, coupled to a power source and configured to be placed in the soil to form a capacitor; and a ground conductive material in direct electrical contact with the soil disposed between the first and second elongate conductive materials, said ground conductive material being coupled to the soil moisture circuit and conductively isolated from the first and second elongate conductive materials.

11. The method of claim 10, wherein the non-conductive substrate comprises a printed circuit board having a head and three coplanar prongs extending downward from the head and wherein the first and second prongs extend downward from opposing sides of the head and the third prong extends downward from the head and between the first and second prongs, and wherein the first and second conductive materials are disposed within the first and second prongs, respectively.

12. The method of claim 11, wherein the probe further comprises third and fourth elongate conductive materials encapsulated in the non-conductive substrate, said third and fourth elongate materials being disposed in the first and second prongs, respectively, and being conductively isolated from the first and second elongate conductive materials and electrically coupled to the soil moisture circuit.

13. The method of claim 12, further comprising simultaneously applying an electrical stimulus to the first and second elongate conductive materials followed a simultaneous electrical stimulus to the third and fourth elongate conductive materials after a predetermined period of time.

14. The method of claim 10, further comprising the steps of:
(i) creating a priority ranking of irrigation zones;
(ii) upon detection that the soil moisture value in more than one irrigation zones has dropped below a threshold value, ranking the irrigation zones where the soil moisture value has dropped below the threshold value according to the priority ranking; and
(iii) opening the irrigation valve corresponding to the irrigation zone having the highest rank in step (ii).

15. The method of claim 10, wherein
the non-conductive substrate comprises a printed circuit board having a head and three coplanar prongs extending downward from the head, the first and second prongs extending downward from opposing sides of the head and the third prong extending downward between the first and second prongs, and wherein the first and third conductive materials are disposed within the first prong and the second and fourth conductive materials are disposed within the second prong, and wherein the ground conductive material is disposed on an outer surface of the third prong.

16. A system for controlling irrigation comprising:
a plurality of wireless transmitters tethered to a plurality of stand-alone soil moisture probes, each of said probes comprising:
first and second elongate conductive materials encapsulated in a non-conductive substrate, said first and second elongate materials coupled to a power source and configured to be placed in the soil to form a capacitor;
a soil moisture circuit encapsulated in the non-conductive substrate coupled to the power source, said circuit having an oscillator for applying an electrical stimulus to the first and second elongate conductive materials;
third and fourth elongate conductive materials encapsulated in the non-conductive substrate, said third and fourth elongate materials being conductively isolated from the first and second elongate conductive materials, coupled to a power source and configured to be placed in the soil to form a capacitor; and
a ground conductive material in direct electrical contact with the soil disposed between the first and second elongate conductive materials, said ground conductive material being coupled to the soil moisture circuit and conductively isolated from the first and second elongate conductive materials;
an irrigation control box equipped with a receiver and a processor, said processor coupled to a plurality of irrigation control valves, each irrigation control valve corresponding to an irrigation zone, wherein at least one soil moisture probe is placed in the soil located in each irrigation zone;
wherein the processor is programmed to convert signal data received from the plurality of transmitters into a soil moisture value, open an irrigation control valve corresponding to the irrigation zone to which the probe corresponds upon detecting that the soil moisture value in the irrigation zone has dropped below a threshold value, and close the irrigation control valve corresponding to the irrigation zone to which the probe corresponds upon detecting that the soil moisture value in the irrigation zone has raised above a threshold value; and
wherein the irrigation control box is configured to receive a signal corresponding to an ambient temperature within an irrigation zone, and upon detecting that the ambient air temperature exceeds a threshold level, the irrigation control box is configured to modify the upper and lower soil moisture threshold values.

17. The system of claim 16 wherein the non-conductive substrate comprises a printed circuit board having a head and three coplanar prongs extending downward from the head, the first and second prongs extending downward from opposing sides of the head and the third prong extending downward between the first and second prongs, and wherein the first and third conductive materials are disposed within the first prong and the second and fourth conductive materials are disposed within the second prong, and wherein the ground conductive material is disposed on an outer surface of the third prong.

* * * * *